(12) United States Patent
Li (10) Patent No.: US 11,622,889 B1
(45) Date of Patent: Apr. 11, 2023

(54) SLEEP HEADSET

(71) Applicant: Shenzhen ZhuoSiJia Trading Co., Ltd., Shenzhen (CN)

(72) Inventor: Nengwen Li, Pingjiang County (CN)

( * ) Notice: Subject to any disclaimer, the term of this patent is extended or adjusted under 35 U.S.C. 154(b) by 0 days.

(21) Appl. No.: 17/726,552

(22) Filed: Apr. 22, 2022

(30) Foreign Application Priority Data

Apr. 14, 2022 (CN) .......................... 202220869686.8

(51) Int. Cl.
*A61F 9/04* (2006.01)
*H04R 1/02* (2006.01)

(52) U.S. Cl.
CPC ............... *A61F 9/04* (2013.01); *H04R 1/025* (2013.01); *A41D 2400/38* (2013.01); *H04R 2201/023* (2013.01)

(58) Field of Classification Search
CPC ..... A61F 9/04; H04R 1/025; H04R 2201/023; A41D 2400/38
See application file for complete search history.

(56) References Cited

U.S. PATENT DOCUMENTS

2017/0157435 A1* 6/2017 Choi ...................... A41D 1/005
2017/0264994 A1* 9/2017 Gordon ................ H04R 1/1091

* cited by examiner

*Primary Examiner* — Andrew L Sniezek (57) ABSTRACT

Embodiments of the present invention provide a sleep headset, which includes: a face slimming strap made of a flexible and elastic breathable material and including a main functioning part that fits a face and a lower mandible on two sides, and first connecting parts extending from two ends of the main functioning part, wherein each of the first connecting parts is provided with a detachable connection structure to enable the face slimming strap to be detachably connected and adjust tightness of the main functioning part against the face and the lower mandible; at least one speaker built in the face slimming strap and disposed at positions corresponding to human ears of a head; and a control box disposed on the face slimming strap or on an eye mask and electrically connected to the speaker. The sleep headset of the present invention can relieve discomfort brought about by the headset during sleep; and moreover, the face slimming strap can realize a face slimming function during sleep.

18 Claims, 11 Drawing Sheets

SLEEP HEADSET

CROSS REFERENCE TO RELATED APPLICATION

This application claims priority benefit of Chinese Patent Application No. 202220869686.8, filed on Apr. 14, 2022, and the entire contents of which are incorporated herein by reference.

TECHNICAL FIELD

The present invention relates to the technical field of daily life products, in particular to a sleep headset.

BACKGROUND

A headset is an electronic device used for play audios and usually a stand-alone device.

People sometimes wear a headset during sleep, but as they fall deeply asleep, they may compress the headset when turning over their heads, causing discomfort to their ears. Therefore, in-ear headsets or headsets with hard housings are not suitable for use during sleep.

SUMMARY

The present invention provides a sleep headset, which aims to solve the above technical problems and also provide functions of face slimming and improving sleep quality during sleep.

The present invention is implemented a sleep headset, including:

a face slimming strap, which is made of a flexible and elastic breathable material and comprises a main functioning part that fits a human face and a lower mandible on two sides, and first connecting parts extending from two ends of the main functioning part;

at least one speaker disposed on the face slimming strap at positions corresponding to human ears of a head; and a control box electrically connected to the speaker and used for controlling the speaker.

Optionally, an eye mask strap, which is made of a flexible material and comprises a mask body for covering human eyes and second connecting parts located at two ends of the mask body and used for fixation to the face slimming strap, the eye mask strap being fixed to the face slimming strap by the second connecting parts.

Optionally, detachable connection structures, which are belt-like extending hook-and-loop fasteners, are disposed on the first connecting parts.

Optionally, the face slimming strap further comprises an anti-snoring part, the anti-snoring part being formed by the main functioning part extending toward a mouth of the human face; the extending anti-snoring part forms a concave space on the main functioning part for supporting a chin part of the human face; and when the first connecting parts are connected and contracted, the anti-snoring part acts on a position of a lower lip of the mouth to maintain a closed state of the mouth.

Optionally, the width of the face slimming strap gradually decreases in directions extending from a middle part to two ends thereof.

Optionally, a width of one side, corresponding to a direction of a forehead, of the eye mask strap is unchanged; and a width of one side, corresponding to a direction of a nose, of the eye mask strap gradually increases while extending from the middle to two ends.

Optionally, each of the first connecting parts is provided with a detachable connection structure to enable the face slimming strap to be detachably connected and adjust tightness of the main functioning part against the face and the lower mandible.

Optionally, the face slimming strap is made of fabrics sewed together and has a structure of multi-layer fabrics.

Optionally, the main functioning part of the face slimming strap is made of fabrics of a mesh structure.

Optionally, the control box is disposed on a side, adjacent to a forehead, of an eye mask strap or disposed at a position, adjacent to a detachable connection structure, on the face slimming strap.

In embodiments of the present invention, the speaker of the headset is built in the face slimming strap. Since the face slimming strap is made of the flexible and elastic breathable material, during sleep, ears will be protected by the face slimming strap, thereby alleviating discomfort caused by hard headset components. At the same time, the face slimming strap in the present invention can squeeze facial fat during sleep; and stretching tension makes two sides of a chin move to left and right sides and an upper side of the face, so as to achieve the purpose of shaping a V-shaped face (specifically, since the fat in cells can flow, the cells will expand due to fat accumulation and shrink due to fat losses, so that long-time compressing of the face with the accumulated fat for proper time can promote the excess fat of the part evenly flow to the body, thereby achieving a face slimming effect).

In a further embodiment, an eye mask strap is also provided, which can play a function of sleep mask during sleep and is beneficial to improving sleep quality.

BRIEF DESCRIPTION OF DRAWINGS

In order to illustrate more clearly embodiments of the present invention or technical schemes in the related art, the drawings used in description of the embodiments or the related art will be briefly described below, and obviously, the drawings in the following description are only some embodiments of the present invention, and for those of ordinary skill in the art, other drawings can be derived on the basis of the structures shown in these drawings without any inventive effort.

DETAILED DESCRIPTION

The technical schemes in the embodiments of the present invention are clearly and completely described in the following with reference to the accompanying drawings in the embodiments of the present invention. It is obvious that the described embodiments are only some of the embodiments of the present invention instead of all the embodiments. All other embodiments obtained by those of ordinary skill in the art based on the embodiments of the present invention without inventive effort are within the scope of the present invention.

The term "embodiment" mentioned in the article means that a particular feature, structure, or characteristic described in connection with the embodiment may be included in at least one embodiment of the present application. The occurrence of the term in various parts in the specification does not necessarily refer to the same embodiment, nor is it an independent or alternative embodiment mutually exclusive of other embodiments. It is understood explicitly and implicitly by those skilled in the art that the embodiments described herein may be combined with other embodiments.

Embodiment I

Figure 1:
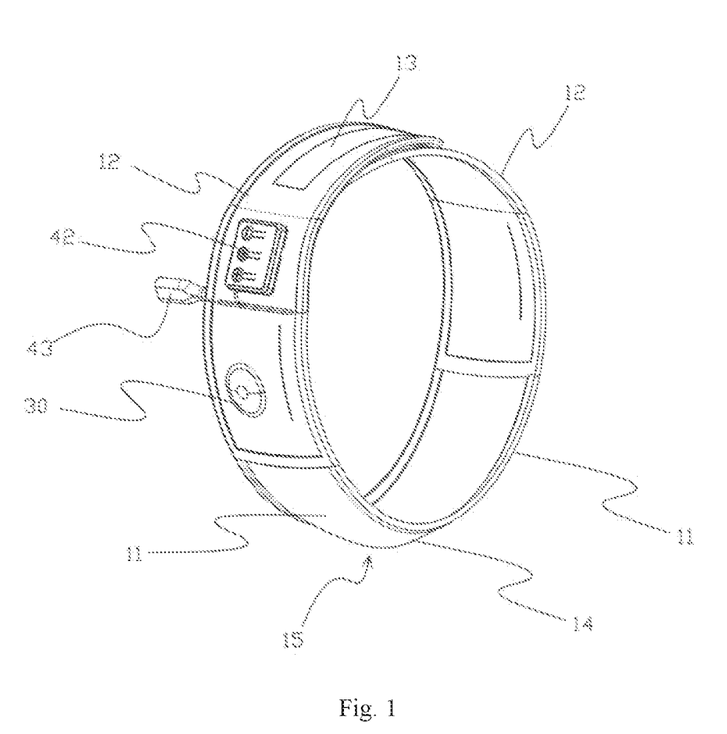
FIG. 1 is a schematic diagram of a sleep headset according to Embodiment I of the present invention.
Figure 2:
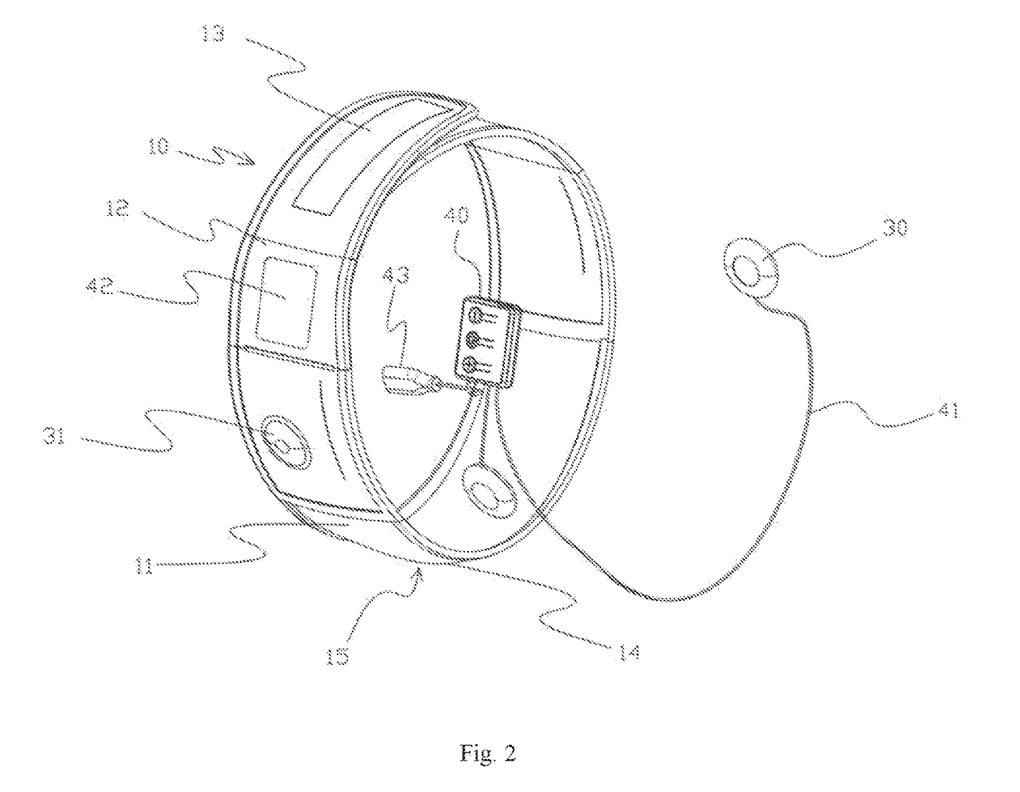
FIG. 2 is a schematic explosion view of the sleep headset according to Embodiment I of the present invention.
Figure 3:
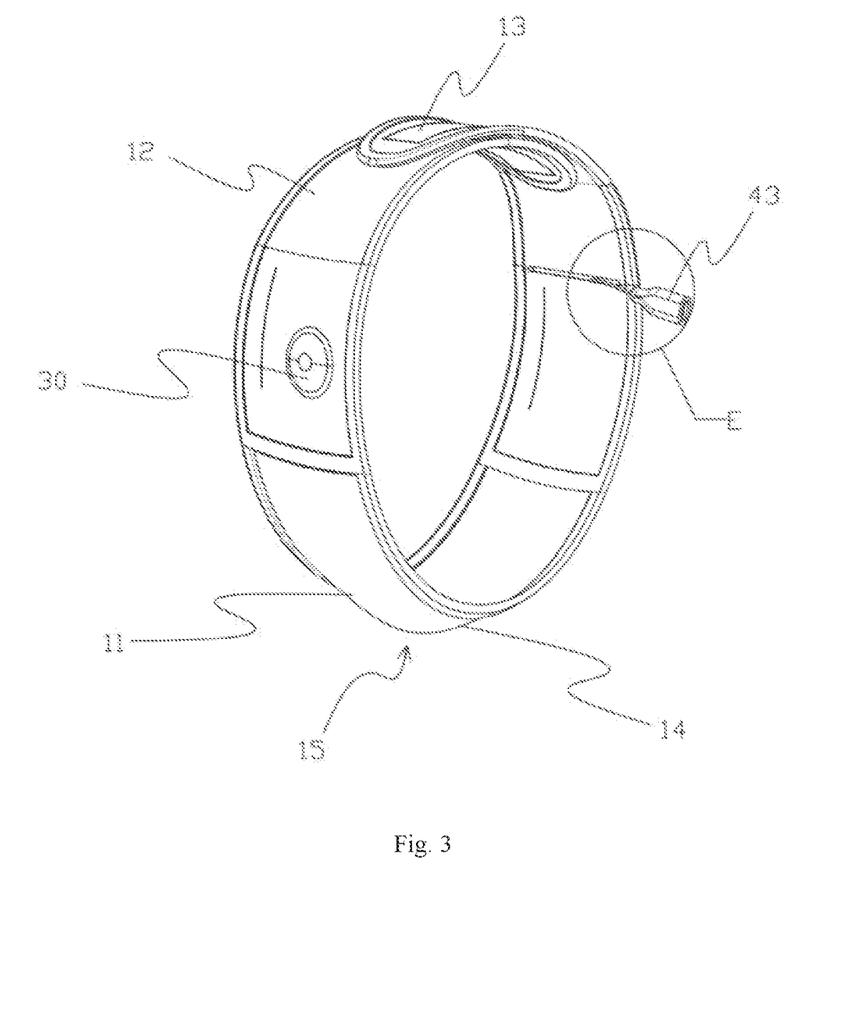
FIG. 3 is a schematic diagram of the sleep headset in another perspective of Embodiment I of the present invention.

As shown in FIGS. 1-3, FIG. 1 is a schematic diagram of a sleep headset according to this embodiment; FIG. 2 is an exploded view of the sleep headset according to this embodiment; and FIG. 3 is a schematic diagram of the sleep headset in another perspective of this embodiment. A sleep headset includes a face slimming strap 10, a speaker 30, and a control box 40.

Here, the face slimming strap 10 is made of a flexible and elastic breathable material, and includes a main functioning part 11 that fits a face and a lower mandible on two sides, and first connecting parts 12 extending from the main functioning part to two ends, wherein each of the first connecting parts 12 is provided with a detachable connection structure 13 to enable the face slimming strap 10 to be detachably connected and adjust tightness of the main functioning part 11 against the face (mainly face areas on two sides) and the lower mandible.

The number of the speakers 30 is at least one, and the at least one speaker is disposed on the face slimming strap 10 at positions corresponding to human ears of a head.

The control box 40 is an apparatus for controlling the speaker 30 to play an audio. A plurality of modules such as communication, storage, playback, and power supply modules are built in the control box 40. The control box 40 is disposed on the face slimming strap 10 or an eye mask strap 20, and is electrically connected to the speaker 30, and in particular, may be electrically connected by a cable 41.

Figure 4:
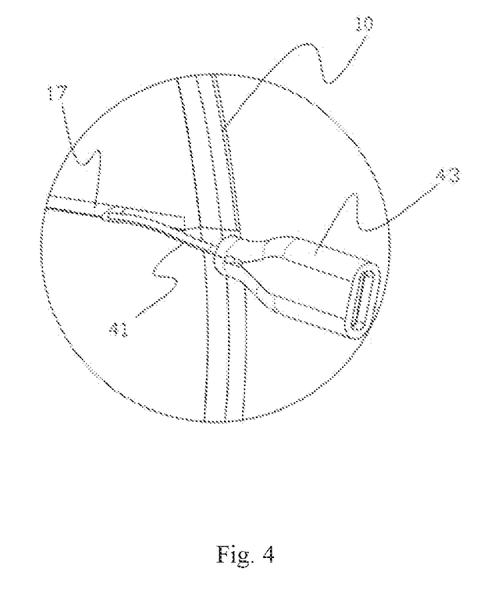
FIG. 4 is an enlarged view of E in FIG. 3.

In an embodiment, As shown in FIGS. 3 and 4, FIG. 4 is an enlarged view of E in FIG. 3. When the control box 40 is provided with a data interface 43, the data interface 43 may be used for data communication; and when the control box 40 is provided with a battery power supply, the data interface 43 may further be used as a charging interface.

As a specific implementation, the control box 40 is disposed in a control box setting area 42 of the first connecting part 12 of the face slimming strap 10; most of the volume of the control box 40 is built in the face slimming strap 10; and a control panel (not shown in the diagram) thereof is exposed to the outside to facilitate control.

The speaker 30 is also built in the face slimming strap 10 at an ear-piece position 31 adjacent to the main functioning part 11. Since the face slimming strap 10 is made of the breathable material, a good sound permeability is enabled. The cable 41 is routed inside the face slimming strap 10, and is connected to the control box 40 and the speaker 30, respectively.

In this embodiment, the detachable connection structures 13 are belt-like extending hook-and-loop fasteners disposed on the first connecting parts 12. Of course, the shape of the hook-and-loop fasteners is not limited: and the belt-like hook-and-loop fastener can withstand greater lateral tension. In other implementations, the detachable connection structure 13 may further be other structures such as a button, a nail buckle and the like that can realize detachable connection, which is not limited to the connection manner proposed in this embodiment.

In this embodiment, the face slimming strap 10 further includes an anti-snoring part 14; the anti-snoring part 14 is formed by the main functioning part 11 extending toward a mouth of the human face; the extending anti-snoring part 14 forms a concave space 15 on the main functioning part 11 for supporting a chin part of the human face. During use, the first connecting parts 12 at two ends of the face slimming strap 10 are tightened and connected by pressing the hook-and-loop fasteners together, and the anti-snoring part 14 acts on a position of a lower lip of a mouth (not covering the lower lip) under the action of pulling force to keep the mouth of a user in a closed state. Since the anti-snoring part 14 can act on the position of the lower lip area of the human body mouth when the face slimming strap 10 is contracted, the human body mouth is always kept in a closed state during sleep, so that an anti-snoring function can be realized.

In this embodiment, the width of the face slimming strap 10 gradually decreases in a direction extending from the middle to the two ends. A main function of the face slimming strap 10 is to realize face slimming and anti-snoring. Therefore, the middle part thereof is a main function realization part; and the two ends mainly exert a connection function. Under the condition of ensuring comfort, the width of the two ends can gradually decreases. In another specific implementation, the width of the main functioning part 11 of the face slimming strap 10 may be unchanged, but the width of the main functioning part 11 may be set in various specifications and models according to needs of different users, so as to meet the needs of the different users.

In this embodiment, the main functioning part 11 and the first connecting parts 12 of the face slimming strap 10 are formed as an integral structure, that is to say, they are made of an integrated flexible and elastic breathable material. In an optional implementation, the face slimming strap 10 is made of fabrics sewed together and has a structure of multi-layer fabrics. The fabric has good air permeability and better comfort of fitting to human skin. The multi-layer structure is conducive to increasing strength and embedding the speaker 30 inside.

In another specific implementation, the main functioning part 11 and the first connecting parts 12 may be connected by sewing, and therefore, the main functioning part 11 and the first connecting parts 12 may be made of different materials. For example, the main functioning part 11 may be made of a woven fabric that is more skin-friendly; and the first connecting parts 12 may be made of a material with better elasticity or flexibility.

As shown in FIG. 4, in a specific implementation, the data interface 43 is also led out to the outside of the face slimming strap 10 through the cable 41. Specifically, a slot 17 is disposed in one side, adjacent to the control box, of the face slimming strap 10. One of functions of the slot 17 is to lead out the data interface 43 from the inside of the face slimming strap 10 through the cable. A further function is that the cable 41 can be hidden in the slot 17 to avoid discomfort caused by the cable pressed against the face during use. The slot 17 in this embodiment is a transverse slot, but is not limited to the manner provided in this embodiment. Slotting may be realized in an oblique or curved manner, and may be set according to a routing direction of the cable 41.

In the embodiment of the present invention, the speaker of the headset is built in the face slimming strap. Since the face slimming strap is made of the flexible and elastic breathable material, during sleep, ears will be protected by the face slimming strap, thereby alleviating discomfort caused by hard headset components. At the same time, the face slimming strap in the present invention can squeeze facial fat during sleep; and stretching tension makes two sides of a chin move to left and right sides and an upper side of the face, so as to achieve the purpose of shaping a V-shaped face (specifically, since the fat in cells can flow, the cells will expand due to fat accumulation and shrink due to fat losses, so that long-time compressing of the face with the accumulated fat for proper time can promote the excess fat of the part evenly flow to the body, thereby achieving a face slimming effect).

Embodiment II

Figure 5:
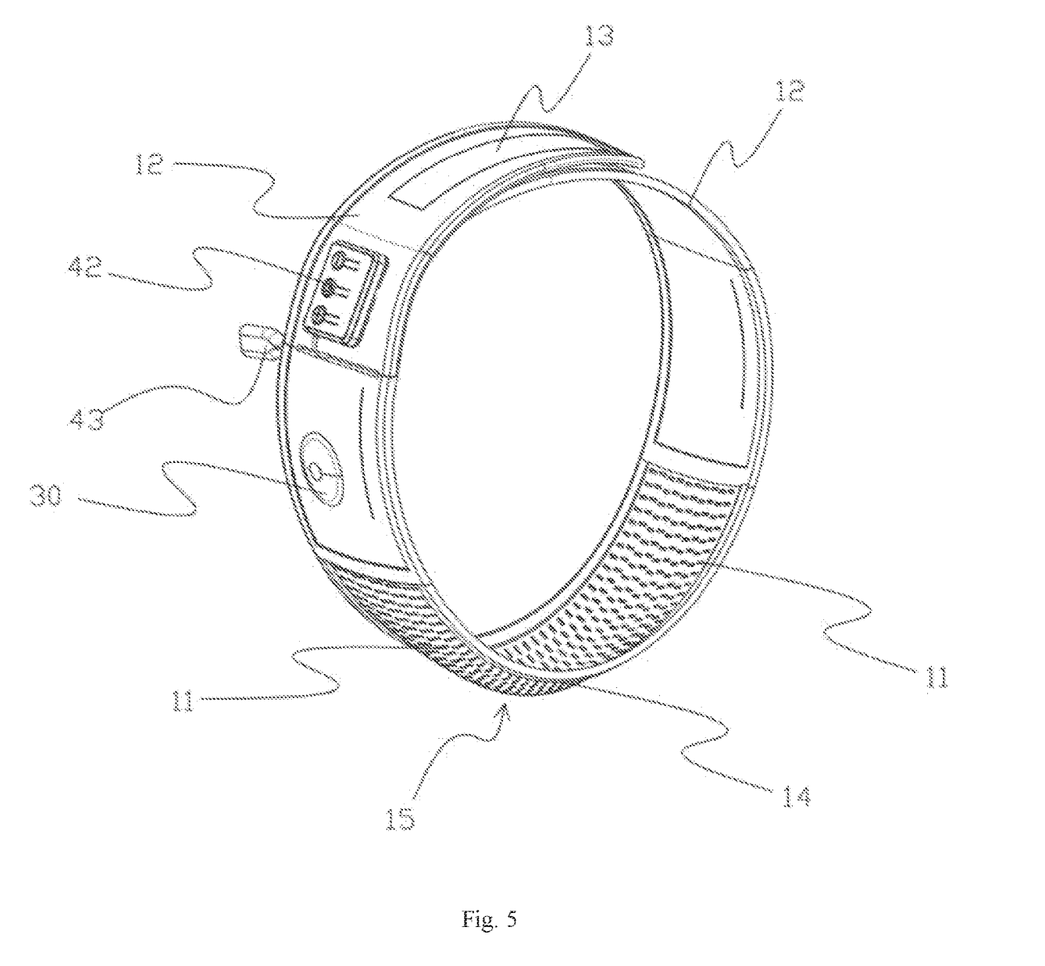
FIG. 5 is a schematic diagram of a sleep headset according to Embodiment II of the present invention.

As shown in FIG. 5, FIG. 5 is a schematic diagram of a sleep headset according to this embodiment. A sleep headset includes a face slimming strap 10, a speaker 30, and a control box 40.

Structures and functions of the face slimming strap 10, the speaker 30 and the control box 40 in this embodiment are the same as those of the face slimming strap 10 described in Embodiment I, which will not be repeated here.

The arrangement of the control box 40 in this embodiment is the same as that of Embodiment I, which will not be described again here.

Here, the face slimming strap 10 is made of a flexible and elastic breathable material, and includes a main functioning part 11 that fits a face and a lower mandible on two sides, and first connecting parts 12 extending from the main functioning part 11 to two ends, wherein each of the first connecting parts 12 is provided with a detachable connection structure 13 to enable the face slimming strap 10 to be detachably connected and adjust tightness of the main functioning part 11 against the face (mainly face areas on two sides) and the lower mandible.

In this embodiment, the first connecting parts 12 and the main functioning part 11 of the face slimming strap 10 differ from each other in their materials and structures. The main functioning part 11 is of a mesh structure, which makes the main functioning part 11 more breathable, and can keep skin dry when acting on the human face for a long time. The main functioning part 11 may be made of a textile material or other flexible materials. The first connecting parts 12 and the main functioning part 11 may be connected by sewing, or connected by other means. Of course, the first connecting parts 12 may alternatively be integrally formed with the main functioning part 11 using the same material.

Embodiment III

Figure 6:
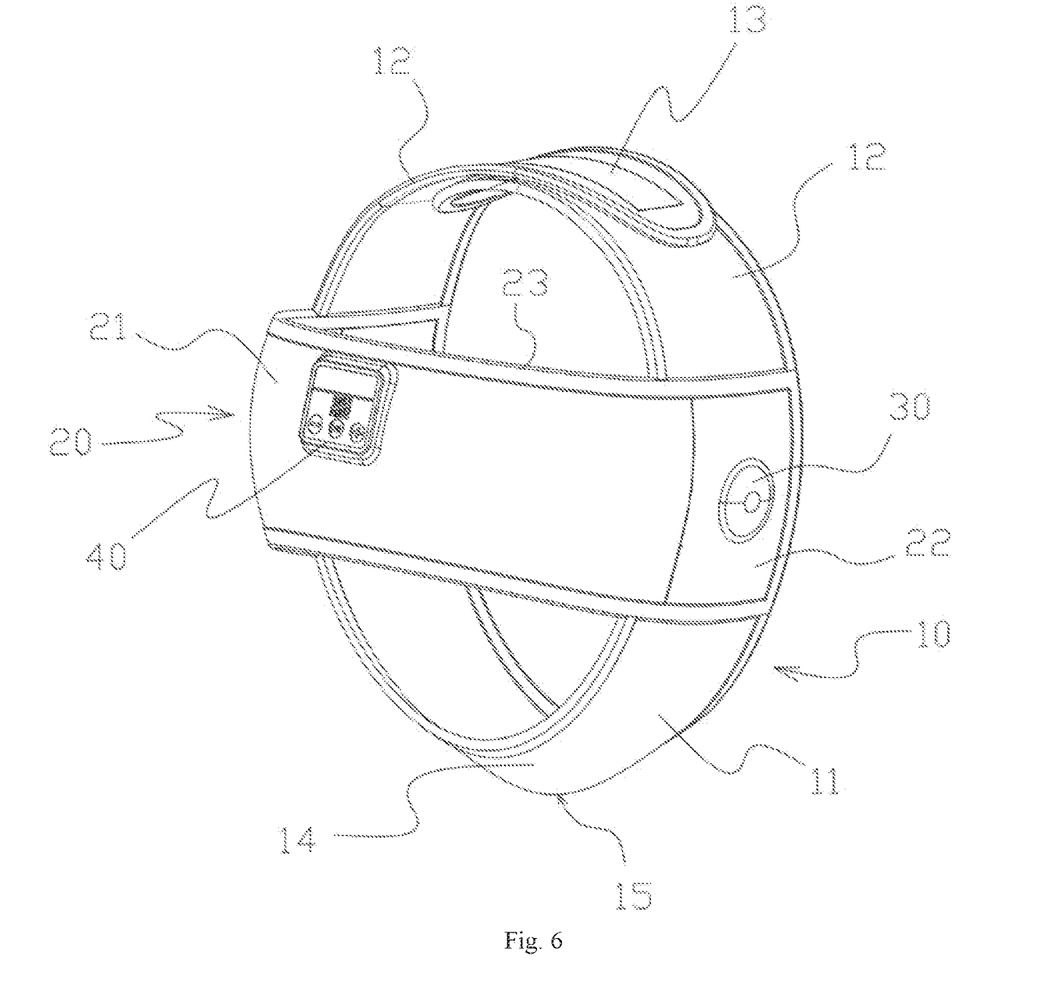
FIG. 6 is a schematic diagram of a sleep headset according to Embodiment III of the present invention.
Figure 7:
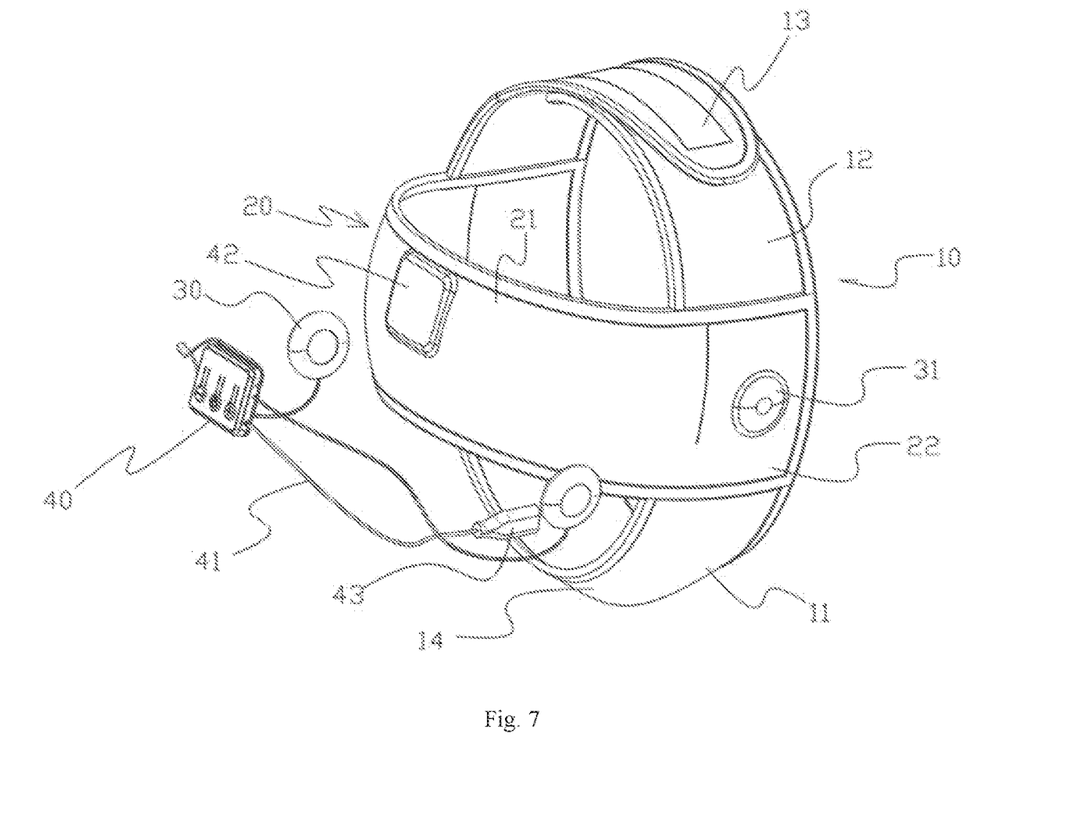
FIG. 7 is an exploded view of the sleep headset according to Embodiment III of the present invention.

As shown in FIGS. 6 and 7. FIG. 6 is a schematic diagram of a sleep headset according to this embodiment; and FIG. 7 is an exploded view of the sleep headset according to this embodiment. A sleep headset includes a face slimming strap 10, an eye mask strap 20, a speaker 30, and a control box 40.

Structures and functions of the face slimming strap 10, the speaker 30 and the control box 40 in this embodiment are the same as those of the face slimming strap 10, the speaker 30 and the control box 40 described in Embodiment I, which will not be repeated here.

Here, the eye mask strap 20 is made of a flexible material, which may be fabrics or other materials with good air permeability. The eye mask strap 20 includes a mask body 21 for covering human eyes and second connecting parts 22 located at two ends of the mask body and used for fixation to the face slimming strap; and the eye mask strap is fixed to the face slimming strap by the second connecting parts.

In this embodiment, the width of the eye mask strap 20 gradually increases in a direction extending from the middle to two ends. Contrary to the face slimming strap 10, a middle area of the eye mask strap 20 is relatively narrow, so that pressure on the bridge of the nose can be avoided.

Further, the width of one side, corresponding to a direction of a forehead, of the eye mask strap 20 is unchanged; and the width of one side, corresponding to a direction of the nose, of the eye mask strap gradually increases while extending from the middle to two ends, so that the area on the side adjacent to the forehead is larger, and the control box 40 can be disposed at the middle part of the eye mask strap 20, adjacent to the side of the forehead.

In a specific implementation, the eye mask strap 20 may also be made by sewing fabrics together, and is fixed to the face slimming strap 10 by sewing.

In a specific implementation, The control box 40 is disposed on the eye mask strap 20, and specifically disposed in the middle area of the eye mask strap 20, so that the hard control box 40 can be prevented from pressing on human eyes to cause discomfort.

Further, the control box 40 is disposed in an area, adjacent to the forehead side, of the eye mask strap 20, so that the control box 40 can be prevented from pressing on the bridge of the nose and causing discomfort.

The cable 41 is routed inside the eye mask strap 20 to electrically connect the control box 40 and the speaker 30. In this embodiment, the eye mask strap 20 may be made of a fabric; an edge of the eye mask strap 20 has a seam edge 23; and the cable 41 is routed along the seam edge 23 as much as possible, so that the middle area of the eye mask strap 20 can be prevented from forming a bumpy texture.

Figure 8:
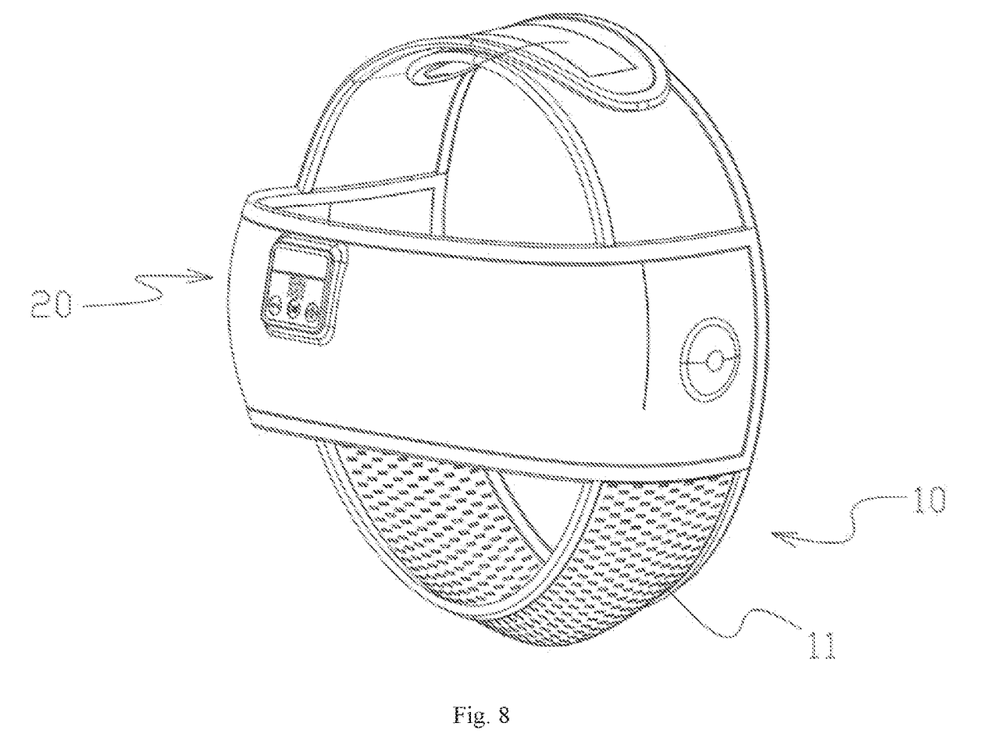
FIG. 8 is another schematic diagram of the sleep headset according to Embodiment III of the present invention.

Further, as shown in FIG. 8, FIG. 8 is a schematic diagram of a sleep headset according to this embodiment. In this embodiment, the first connecting parts 12 and the main functioning part 11 of the face slimming strap 10 differ from each other in their materials and structures. The main functioning part 11 is of a mesh structure, which makes the main functioning part 11 more breathable, and can keep skin dry when acting on the human face for a long time. The main body functional part 11 may be made of a textile material or other flexible materials; and the first connecting parts 12 and the main body functional part 11 may be connected by sewing, or connected by other means. Of course, the first connecting parts 12 may alternatively be integrally formed with the main functioning part 11 using the same material.

Embodiment IV

Figure 9:
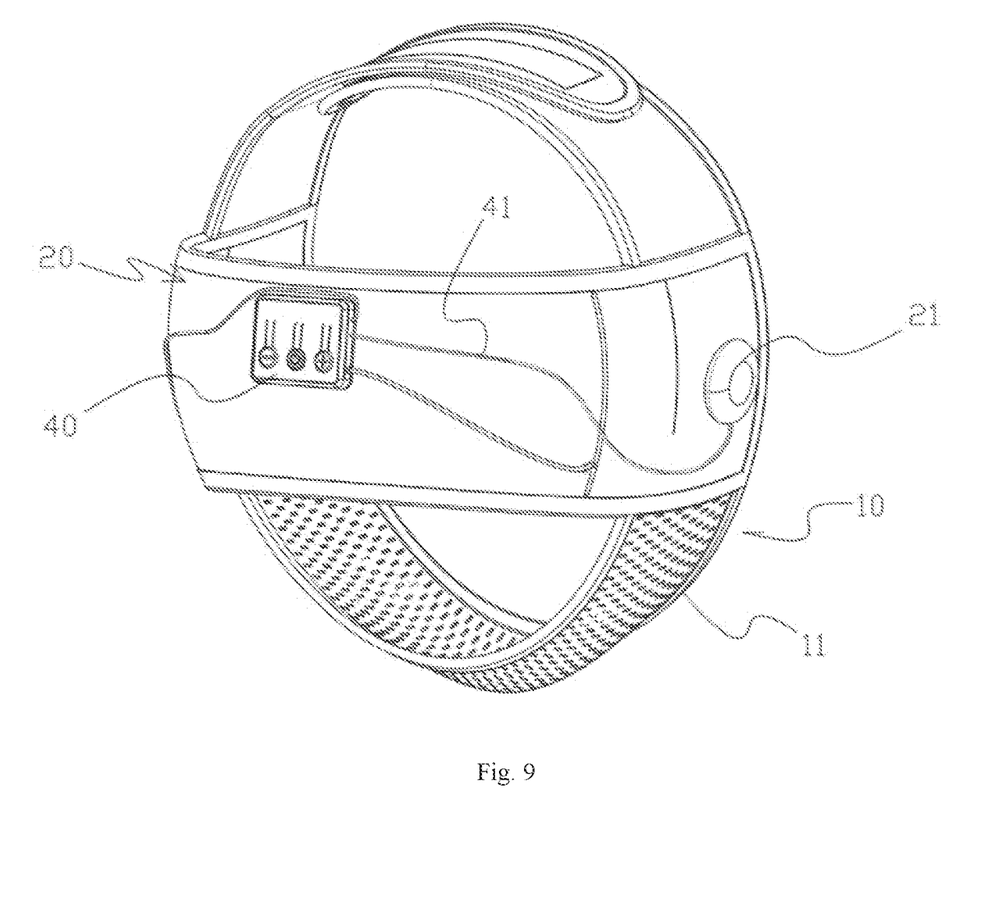
FIG. 9 is a schematic diagram of a sleep headset according to Embodiment IV of the present invention.

As shown in FIG. 9, FIG. 9 is a schematic diagram of a sleep headset according to this embodiment. A sleep headset includes a face slimming strap 10, an eye mask strap 20, a speaker 30, and a control box 40.

Structures and functions of the face slimming strap 10, the speaker 30 and the control box 40 in this embodiment are the same as those of the face slimming strap 10, the speaker 30 and the control box 40 described in Embodiment I or Embodiment II or Embodiment III, which will not be repeated here. The difference is that the arrangement of the control box 40 and the speaker 30 is different from that in the above embodiments.

Specifically, the control box 40 is disposed outside the eye mask strap 20; the speaker 30 is disposed outside the face slimming strap 10; and the control box 40 and the speaker 30 are connected by a cable 41 disposed on the outer surface of the eye mask strap 20. The control box 40 is connected to a data interface (not shown in the diagram) via another cable. By disposing the control box 40, the speaker 30, and the cable 41 outside the eye mask strap 20, discomfort caused by an increase in the local thickness of the eye mask strap can be prevented. The cable 41 and the control box 40, which are attached to the outside of the eye mask strap 20, are not affected by the pulling force of the eye mask strap 20, and do not exert a pressure on the eye mask strap 20, so that the comfort of the eye mask strap 20 is improved.

Figure 10:
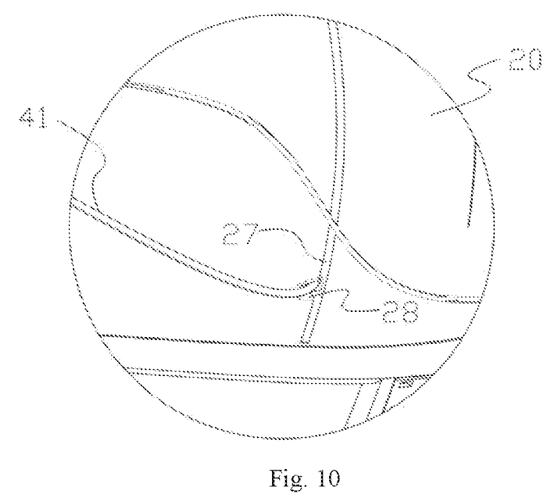
FIG. 10 is an enlarged view of F in FIG. 9.

In this embodiment, as shown in FIG. 10, FIG. 10 is a schematic diagram of leading out the data interface through the cable 41 on the eye mask strap 20. The data interface is led out from the inner side of the eye mask strap 20. Therefore, a lead groove 27 is disposed in the eye mask strap 20. The lead groove 27 is opened to a downward edge direction from an upper edge of the eye mask strap 20. At the same time, a limiting groove 28 intersecting therewith is further disposed. Discomfort caused by leading-out of the cable 41 can be reduced by arrangement of the lead groove 27.

Figure 11:
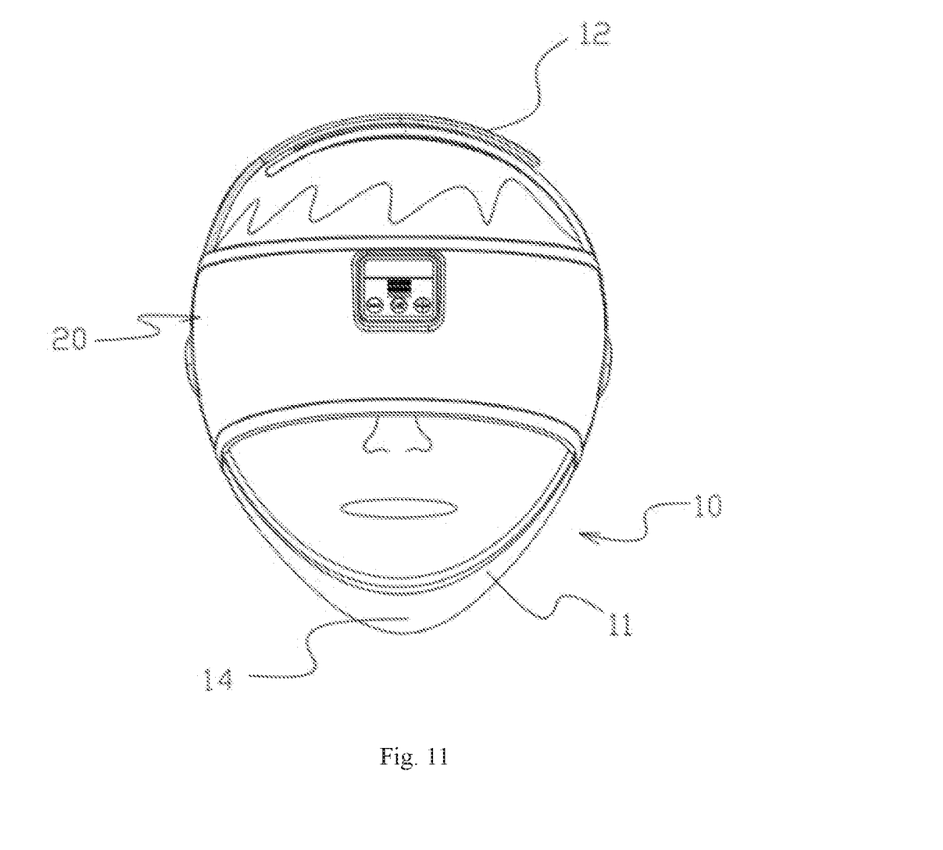
FIG. 11 is a schematic diagram of the sleep headset in use according to Embodiment III of the present invention.

As shown in FIG. 11, FIG. 11 is a schematic diagram of the sleep headset in use in Embodiment III. Before use, the first connecting parts 12 at two ends of the face slimming strap 10 are disconnected. During use, the face slimming strap 10 is attached to two sides of the human face and the lower mandible; the first connecting parts 12 at two ends are pulled to a suitable position; and then the first connecting parts 12 at two ends are joined to each other by hook-and-loop fasteners; the main functioning part 11 of the face slimming strap 10 generates a certain pressure on the human face on two sides; and the anti-snoring part 14 forms a pressure on the mouth to keep the mouth in a closed state. The eye mask strap 20 can be moved up to the forehead before use, and can be moved down during sleep to cover eyes and realize a function of a sleep mask. Based on structural similarity of the various embodiments, for the use process of the sleep headsets of other embodiments, the use process in Embodiment III can be referred to, which will not be repeated here.

The sleep headset provided by the embodiments of the present application are described in detail above. The principles and implementations of the present application are described herein by using specific examples. The description of the above embodiments is only used to help understand the method of the present application and core ideas thereof. Moreover, for those skilled in the art, according to the idea of the present application, changes to the specific implementations and application range are possible. To sum up, the content of this specification should not be understood as a limitation to the present application.

The invention claimed is:

1. A sleep headset, comprising:
   a face slimming strap, which is made of a flexible and elastic breathable material and comprises a main functioning part that fits a human face and a lower mandible on two sides, and further comprises first connecting parts extending from two ends of the main functioning part;
   at least one speaker connected to the face slimming strap and disposed at positions corresponding to human ears of a head; and
   a control box electrically connected to the speaker through a cable and used for controlling the speaker;
   wherein the face slimming strap is of a substantially elongated rectangular shape in an expanded state;
   the main functioning part and the first connecting parts are connected by sewing, and wherein the main functioning part is made of a woven fabric that is relatively more skin-friendly in comparison with the first connecting parts, and wherein the first connecting parts are made of a material with relatively greater elasticity or flexibility in comparison with the main functioning part.

2. The sleep headset of claim 1, further comprising an eye mask strap, which is made of a flexible material and comprises a mask body used for covering human eyes and second connecting parts located at two ends of the mask body and used for fixation to the face slimming strap, the eye mask strap being fixed to the face slimming strap by the second connecting parts.

3. The sleep headset of claim 2, wherein a width of one side, corresponding to a direction of a forehead, of the eye mask strap is unchanged; and a width of one side, corresponding to a direction of a nose, of the eye mask strap gradually increases in the direction of extending from the middle of the eye mask strap to two ends of the eye mask strap.

4. The sleep headset of claim 2, wherein the control box is disposed on a side of an eye mask strap adjacent to a forehead of a user.

5. The sleep headset of claim 4, wherein the cable is routed inside the eye mask strap to electrically connect the control box to the at least one speaker, wherein an edge of the eye mask strap has a seam edge, and the cable is routed along the seam edge as much as possible so that the middle portion of the eye mask strap is prevented from forming a bumpy texture.

6. The sleep headset of claim 4, wherein a data interface is led out from an inner side of the eye mask strap through another cable in the eye mask strap, wherein a lead groove is defined in the eye mask strap and runs from an upper edge of the eye mask strap to a lower edge of the eye mask strap, and wherein a limiting slot is further defined in the eye mask strap and intersect the lead groove, so that the other cable is hidden inside the lead groove to reduce discomfort caused by leading-out of the other cable.

7. The sleep headset of claim 2, wherein the control box is disposed on an outer side of the eye mask strap, the at least one speaker is disposed on an outer side of the face slimming strap, and wherein the control box is connected to the at least one speaker through a cable disposed on an outer surface of the eye mask strap.

8. The sleep headset of claim 2, wherein the control box is disposed on the eye mask strap in a middle portion of the eye mask strap thus preventing the control box from pressing on human eyes to cause discomfort.

9. The sleep headset of claim 1, wherein the first connecting parts are detachable connection structures, which are belt-like extending hook-and-loop fasteners.

10. The sleep headset of claim 9, wherein the control box is disposed on the face slimming strap at a position adjacent to a respective detachable connection structure.

11. The sleep headset of claim 1, wherein the face slimming strap further comprises an anti-snoring part, the anti-snoring part being formed by the main functioning part extending toward a mouth of the human face; the extending anti-snoring part forms a concave space on the main functioning part for supporting a chin part of the human face; and when the first connecting parts are connected and contracted, the anti-snoring part acts on a position of a lower lip of the mouth to maintain a closed state of the mouth.

12. The sleep headset of claim 1, wherein a width of the face slimming strap gradually decreases in directions extending from a middle part to two ends thereof.

13. The sleep headset of claim 1, wherein a user's nostrils are exposed out of the sleep headset during use.

14. The sleep headset of claim 1, wherein the control box is mostly built inside the face slimming strap, and wherein the control box comprises a control panel exposed out of the face slimming strap to facilitate control.

15. The sleep headset of claim 1, wherein the cable is routed inside the face slimming strap.

16. The sleep headset of claim 1, wherein the main functioning part is of a net structure with a plurality of breather holes.

17. A sleep headset, comprising:
- a face slimming strap, which is made of a flexible and elastic breathable material and comprises a main functioning part that fits a human face and a lower mandible on two sides, and further comprises first connecting parts extending from two ends of the main functioning part;
- at least one speaker connected to the face slimming strap and disposed at positions corresponding to human ears of a head; and
- a control box electrically connected to the speaker through a cable and used for controlling the speaker;
- wherein the face slimming strap is of a substantially elongated rectangular shape in an expanded state;
- a data interface is led out of the face slimming strap through another cable, wherein a groove is defined in the face slimming strap adjacent to the control box and is configured to lead out the data interface from an inside of the face slimming strap through the other cable, and wherein the other cable is hidden inside the groove to avoid discomfort caused by the cable pressed against a user's face during use.

18. A sleep headset, comprising:
- a face slimming strap, which is made of a flexible and elastic breathable material and comprises a main functioning part that fits a human face and a lower mandible on two sides, and further comprises first connecting parts extending from two ends of the main functioning part;
- an eye mask strap;
- at least one speaker connected to the face slimming strap and disposed at positions corresponding to human ears of a head; and
- a control box electrically connected to the speaker through a cable and used for controlling the speaker;
- wherein the eye mask strap is made of a flexible material and comprises a mask body used for covering human eyes and second connecting parts located at two ends of the mask body and used for fixing to the face slimming strap, the eye mask strap being fixed to the face slimming strap by the second connecting parts;
- wherein the face slimming strap is of a substantially elongated rectangular shape in an expanded state;
- a width of one side, corresponding to a direction of a forehead, of the eye mask strap is unchanged; and a width of one side, corresponding to a direction of a nose, of the eye mask strap gradually increases in the direction of extending from the middle of the eye mask strap to two ends of the eye mask strap.

* * * * *